United States Patent
Kramann

(10) Patent No.: US 9,999,432 B2
(45) Date of Patent: Jun. 19, 2018

(54) SNARE DEVICE FOR CATCHING AN OBJECT

(71) Applicant: PFM MEDICAL AG, Cologne (DE)

(72) Inventor: Bernhard Kramann, Homburg/Saar (DE)

(73) Assignee: PFM MEDICAL AG, Cologne (DE)

( * ) Notice: Subject to any disclaimer, the term of this patent is extended or adjusted under 35 U.S.C. 154(b) by 70 days.

(21) Appl. No.: 15/100,014

(22) PCT Filed: Nov. 24, 2014

(86) PCT No.: PCT/EP2014/075388
§ 371 (c)(1),
(2) Date: May 27, 2016

(87) PCT Pub. No.: WO2015/078806
PCT Pub. Date: Jun. 4, 2015

(65) Prior Publication Data
US 2017/0007278 A1    Jan. 12, 2017

(30) Foreign Application Priority Data
Nov. 29, 2013 (DE) .................... 20 2013 105 451 U

(51) Int. Cl.
*A61B 17/22* (2006.01)
*A61B 17/221* (2006.01)
(Continued)

(52) U.S. Cl.
CPC ............ *A61B 17/221* (2013.01); *A61B 17/50* (2013.01); *A61B 2017/00358* (2013.01);
(Continued)

(58) Field of Classification Search
CPC ................. A61B 17/221; A61B 17/50; A61B 2017/00358; A61B 2017/22035;
(Continued)

(56) References Cited

U.S. PATENT DOCUMENTS 5,171,233 A * 12/1992 Amplatz .............. A61B 17/221
604/540
5,342,371 A    8/1994 Welter et al.
(Continued)

FOREIGN PATENT DOCUMENTS

CN    101389289    3/2009
DE    19514534     10/1996
(Continued)

OTHER PUBLICATIONS

English translation of International Search Report from corresponding PCT application No. PCT/EP2014/075388 dated Feb. 5, 2015.

*Primary Examiner* — Son Dang
(74) *Attorney, Agent, or Firm* — Grossman, Tucker, Perreault & Pfleger, PLLC

(57) ABSTRACT

The invention relates to a snare device for catching an object, in particular for catching objects or foreign bodies in a human or animal body, comprising a hollow element, in particular a catheter, and a snare of a flexible elastic shape-memory material, wherein the snare can be moved relative to the hollow element and can be pulled into the hollow element and can be pushed out of the hollow element, and wherein the snare has a memorized original shape, to which the snare returns, when the snare is pushed out of the hollow element, by means of the material stresses caused when the snare is pulled in, and the hollow element has an outlet opening, which is arranged laterally on the hollow element and which is set back from the distal end of the hollow element and through which the snare can be pushed out of the hollow element and can be pulled into the hollow element.

19 Claims, 8 Drawing Sheets

(51) Int. Cl.
*A61B 17/50* (2006.01)
*A61B 17/00* (2006.01)

(52) U.S. Cl.
CPC ............... *A61B 2017/00867* (2013.01); *A61B 2017/00871* (2013.01); *A61B 2017/2212* (2013.01); *A61B 2017/22035* (2013.01)

(58) Field of Classification Search
CPC A61B 2017/00871; A61B 2017/00867; A61B 2017/2212
See application file for complete search history.

(56) References Cited

U.S. PATENT DOCUMENTS

| | | | | |
|---|---|---|---|---|
| 5,562,678 | A * | 10/1996 | Booker | A61B 17/29 606/106 |
| 5,613,973 | A * | 3/1997 | Jackson | A61B 17/0218 606/1 |
| 5,643,281 | A * | 7/1997 | Suhocki | A61B 17/32056 606/106 |
| 6,093,195 | A * | 7/2000 | Ouchi | A61B 18/14 604/22 |
| 6,966,914 | B2 * | 11/2005 | Abe | A61B 17/221 606/106 |
| 8,974,470 | B2 * | 3/2015 | Lampropoulos | A61B 17/221 606/113 |
| 9,039,713 | B2 * | 5/2015 | Segermark | A61B 17/221 606/113 |
| 2002/0188262 | A1 * | 12/2002 | Abe | A61B 17/221 604/326 |
| 2005/0209609 | A1 * | 9/2005 | Wallace | A61B 17/221 606/113 |
| 2007/0118165 | A1 * | 5/2007 | DeMello | A61B 17/221 606/159 |
| 2007/0260264 | A1 * | 11/2007 | Nobis | A61B 17/32056 606/113 |
| 2012/0029526 | A1 * | 2/2012 | Hewitt | A61B 17/00234 606/113 |
| 2013/0035699 | A1 * | 2/2013 | Heneveld | A61B 17/0057 606/144 |

FOREIGN PATENT DOCUMENTS

| | | |
|---|---|---|
| DE | 19938902 | 4/2000 |
| DE | 102006053448 | 6/2008 |
| EP | 1974692 | 1/2008 |
| EP | 1974692 | 10/2008 |
| EP | 2052688 | 4/2009 |
| EP | 2489313 | 8/2012 |
| WO | 00/16703 | 3/2000 |
| WO | 2011/094261 | 8/2011 |

* cited by examiner

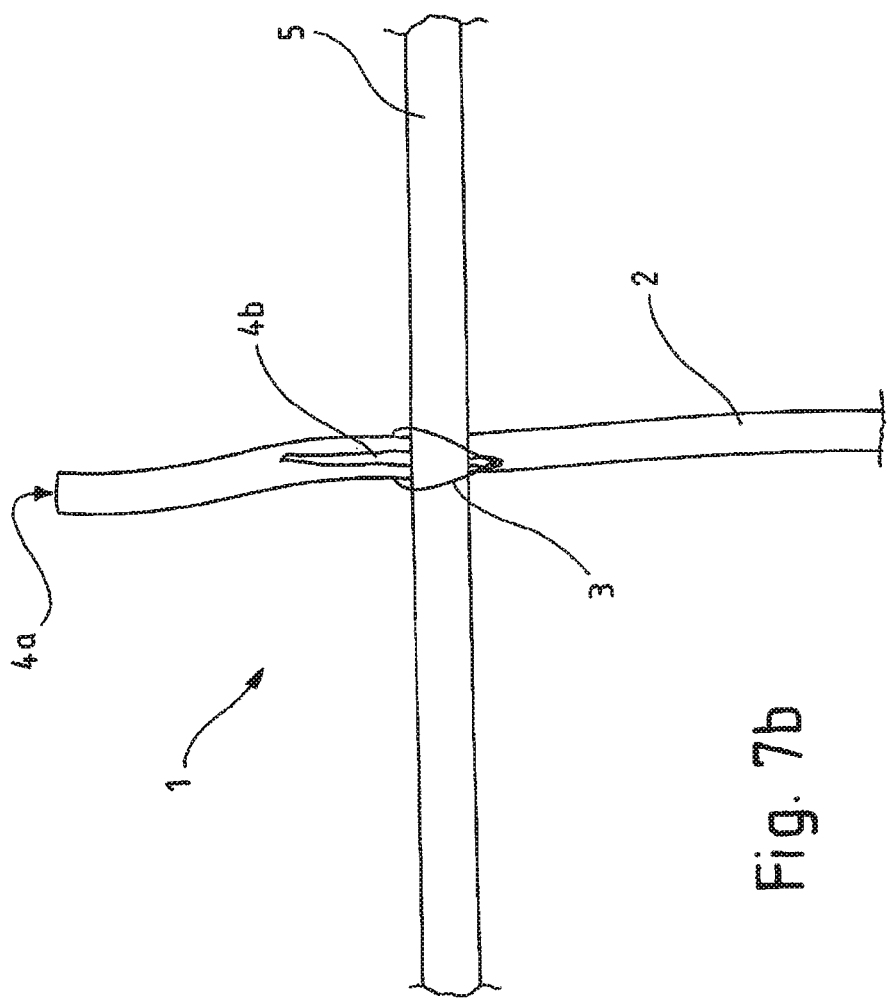

SNARE DEVICE FOR CATCHING AN OBJECT

FIELD OF THE INVENTION

The invention relates to a snare device for catching an object, in particular for catching objects or foreign bodies in a human or animal body, comprising a hollow element, in particular a catheter, and a snare of a flexible elastic shape-memory material, wherein the snare can be moved relative to the hollow element and can be pulled into the hollow element and can be pushed out of the hollow element, and wherein the snare has a memorized original shape, to which the snare returns, when the snare is pushed out of the hollow element, by means of the material stresses caused when the snare is pulled in.

Snare devices for catching objects made of shape-memory material, which are kept in a hollow element and movable relative to it, are known from the prior art.

BACKGROUND

In DE 195 14 534 C2 and EP 1 113 755 B1 catching snares are described, which enable the extraction of objects out of a human or animal body by a minimal-invasive procedure. These devices each have a snare of shape-memory material, which can be put around an object to be extracted. If the object to be caught is enclosed by the snare, the snare is tightened, whereby the object is held by the snare and the object can be extracted. Using such catching snares, objects, in particular fragments of catheters or of guide wires, can be caught in many different directions. The requirement for the catching is that the snare can be laid around the object. For this purpose the object needs an accessible end, over which end the snare can be put. Objects, which ends are not accessible in the following referred to as non-probable, cannot be extracted by using these catching snares.

Probable in the sense of the invention therefore means that an object to be caught is catchable by the catching snare. For this purpose the object needs an accessible end, which end can be grasped by the snare respectively over which end the snare can be laid. The snare is tightened so that the object is enclosed by the snare firmly. By withdrawing the snare respectively the snare device, the object can be extracted out of the human or animal body. The term "probable" is used in the following in the aforementioned matter.

Furthermore, EP 2 052 688 B2 and DE 10 2006 053 448 A1 disclose snare devices, which have a locking wire, which can be pushed through the snare of the snare device to catch an object between a part of the snare and the locking wire extending through the snare. Using such snare devices objects can be caught, which ends are non-probable. The snare is positioned besides the object to be caught and the locking wire encloses the object on the opposite side of the object, wherein the locking wire engages with the snare, so that the snare and the locking wire surround the object. The object is caught and can be extracted. For such snare devices it is disadvantageous that the hollow elements used with these snare devices have a large diameter, because these snare devices have in addition to the snare a locking wire.

The daily clinical routine has shown that situations, in which ends of objects to be extracted are non-probable are relatively common. This applies to about every tenth procedure. By using a so-called pigtail catheter, which has to be inserted separately, it can be tried to hook the end of the pigtail catheter to the object, for instance a fragment of a catheter, and to execute a pulling motion afterwards so that it is maybe possible to probe the object by moving the end of the object in an open area. The open area can be for example provided by an adjacent vein or a body orifice.

To catch or extract objects, whose ends are non-probable, from the prior art particularly for this application developed pincers respectively special catching snares are known for the objects. These special instruments are exclusively designed for the aforementioned application for objects with non-probable ends. They have special hooks respectively hook-shaped snares, with which the object can be hooked and a fixation of the object by a locking wire can be done afterwards. The locking wire interlaces between the object and the hook-shaped snare so that the object is locked and can be retrieved.

The solutions known from the prior art have the disadvantage that these special instruments for catching of objects with non-probable ends are used only after the catching with conventional snare devices is failed, thus an object with non-probable ends is on hand. Therefore, at first, the conventional snare device has to be removed from the human or animal body and the special instrument has to be inserted separately. Here from derives another disadvantage, which is based on the fact that the caliber of the special instrument is larger than the caliber of the conventional snare device. This enlarges the puncture site, which can lead to complications at the puncture site. The consequence can be the development of thrombosis and/or of hardly stoppable secondary bleedings.

Based on the aforementioned prior art it is the object of the invention to enhance the capability of the known snare devices, in particular to provide the possibility to catch objects with non-probable ends in addition to catch object with probable ends.

SUMMARY

It is another object of the invention to provide a snare device, which caliber is small even for the case of catching objects, whose ends are non-probable, in particular to avoid complications for a patient, whereby said complications can be evoked by a large caliber of the snare devices.

For technically solving this object according to the invention a snare device of the previously mentioned kind is suggested, which is characterized in that the hollow element has an outlet opening, which is arranged laterally on the hollow element and which is set back from the distal end of the hollow element and through which the snare can be pushed out of the hollow element and can be pulled into the hollow element.

The invention is based on the finding that during the catching of objects with non-probable ends the grasping around an object with an additional wire, for instance a guide wire or a locking wire or similar mechanism is not necessary, but rather it can be performed with the hollow element itself. Consequently, with the suggested solution it is possible to catch objects with probable ends as well as to catch objects with non-probable ends. Therefore, the use of special instruments designed for this purpose and known from the prior art can be waived. The advantage resulting from this is that the used hollow element has a smaller diameter, since no additional channel for the guide wire or locking wire is necessary.

As a snare of the snare device it is suggested to use the known snare proposed in EP 1 113 755 B1. This snare is at least partly double-laid and forms two snare parts that mutually align in such a manner that they have an inner opening and in particular this surrounding columns in an impressed configuration. In addition, the plane of the snare in the impressed configuration is bent at an angle relative to the hollow element used with the snare.

A preferred embodiment provides that the snare is rotatable by 360° relative to the hollow element. By rotating the snare it can be manipulated in such a manner that it either exits the distal outlet opening positioned at the end of the hollow element or exits the lateral outlet opening of the hollow element. In the cases where the ends of objects to be caught are non-probable the snare is pushed out of the lateral outlet opening of the hollow element by the surgeon and the hollow element is moved in such a position that the object to be caught is arranged in between the hollow element and the emerged snare. To catch the object, the snare is pulled into the hollow element in such a manner that the snare is laid over the hollow element, so that the object to be caught is grasped around and locked.

Advantageously, the snare is rotatable by a manipulation device, in particularly by a torquer, which is arranged at the proximal end of the snare. In addition the snare can be pulled into the hollow element and be pushed out of it by the manipulation device. The use of such a manipulation device facilitates the handling of the snare, because the snare consists usually of a very thin material. In the manipulation device itself, the snare is locked by clamping means. These can be released if the manipulation device is no longer needed.

A further embodiment of the invention provides that the lateral outlet opening of the hollow element is set back from the distal end of the hollow element by about 1 cm to about 3 cm, preferably by about 2 cm. This ensures an adequate distance between the lateral outlet opening and the distal end of the hollow element so that the hollow element can be used for locking respectively for grasping around objects with non-probable ends by the device according to the invention. A preferred embodiment of the invention provides that the lateral outlet opening of the hollow element is formed in the shape of an elongated slot. Such shaping of the lateral outlet opening facilitates the emergence of the snare out of the lateral outlet opening of the hollow element.

In a further embodiment, the shape-memory material of the snare consists of metal, in particular nitinol, or of plastics.

Advantageously, the hollow element has a diameter of about two French to about eight French, preferably of about four French to about six French. The diameter of the hollow element used with the snare device is therefore significantly smaller than the diameter of special instruments for catching objects respectively foreign bodies with non-probable ends known from the prior art. A substantial advantage of the smaller diameter of the hollow element is that complications at the puncture site, which may occur with hollow elements of larger diameter, can be avoided. In particular, the risk of occurring thrombosis and/or hardly stoppable secondary bleedings at the puncture site can be reduced.

The inventive snare device has a marker at the snare, to make the snare visible under displaying devices. During the execution of a surgery, therefore, to retrieve respectively catch an object respectively a foreign body and extract it, it is advantageous if the snare has a marker, which makes the snare visible under a displaying device. This is possible, for example, by the use of a fluoroscope, an MRI respectively through other electronic displaying devices, which make markers at the snare visible by, for instance, an x-ray machine or a sonography. The markers themselves can, for example, be magnetic resonance markers.

Further details, features and advantages of the invention will be explained with respect to the embodiment shown in the figures.

BRIEF DESCRIPTION OF THE DRAWINGS

FIGS. 7a and 7b are the inventive snare device with a laterally caught foreign body.

DETAILED DESCRIPTION

Figure 1:
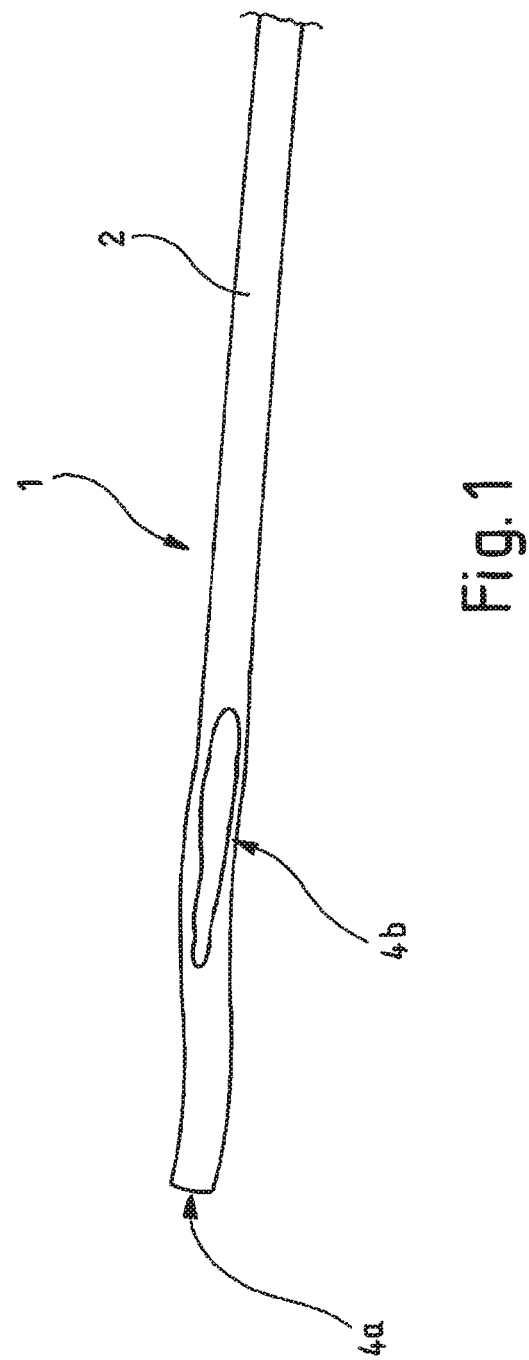
FIG. 1 is an embodiment of a catheter according to the invention.

In FIG. 1, a catheter (2) of an embodiment of an inventive snare device (1) is shown in a side view. The catheter (2) has in addition to the outlet opening (4a) at the a lateral outlet opening (4b). The lateral outlet opening (4b) is in the form of an elongated slot. The snare (3) is arranged completely in the catheter (2).

Figure 2:
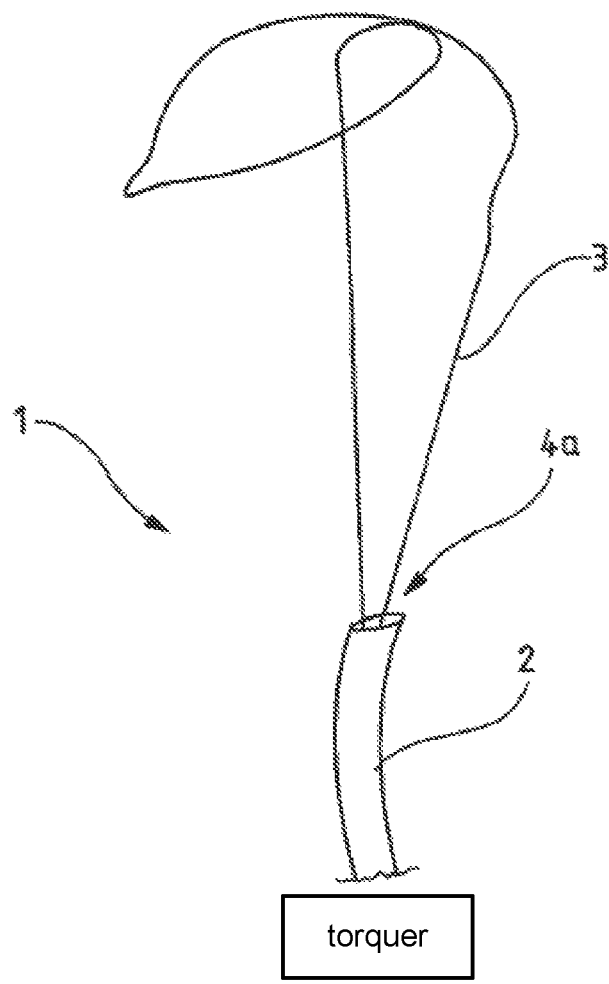
FIG. 2 is an embodiment of a snare device according to the invention, with a snare completely emerged out of the end opening of the catheter.

In FIG. 2 the snare device (1) is shown, wherein the snare (3) of the snare device (1) is completely emerged out of the outlet opening (4a) at the end of the catheter (2). This represents the conventional emergence, which is known from the prior art of EP 1 113 755 B1.

When the snare (3) is emerged out of the outlet opening (4a) at the end of the catheter (2), foreign bodies to be caught, such as catheter fragments, wires or the like may be caught solely, if they have an accessible end, which is probable by the snare (3). For this, the snare (3) is laid over the foreign body (5) to be caught and brought back into the catheter (2), whereby the snare (3) tightens and grasps around the foreign body (5). The foreign body (5) can then be extracted.

If the foreign body (5) is not catchable in this manner and has therefore no free accessible end, the snare (3) is pulled back into the catheter (2) and is manipulated by means of a torquer, which is arranged at the proximal end of the snare (3) and allows an examiner respectively a surgeon to rotate the snare (3) in relation to the catheter (2) and to pull the snare (3) into the catheter (2) respectively to push it out of the catheter (2), in such a manner that the snare (3) now emerges out of the lateral outlet opening (4a) of the catheter (2). This is illustrated in FIG. 3

The snare (3) in its memorized original shape (see FIG. 2) is formed such that the elongated proximal portion of the snare (3) is angled in a predetermined angle. This angulation and the tendency of the shape-memory material of the snare (3) to return back into the memorized original shape, the snare (3) can be manipulated such that an emergence of the snare (3) out of the lateral outlet opening (4b) is possible, or if this is not desired, be manipulated by a rotation at the torquer such that the snare (3) does not emerge out of the lateral outlet opening (4b) of the catheter (2), but from the outlet opening (4a) at the end of the catheter (2).

Figure 3:
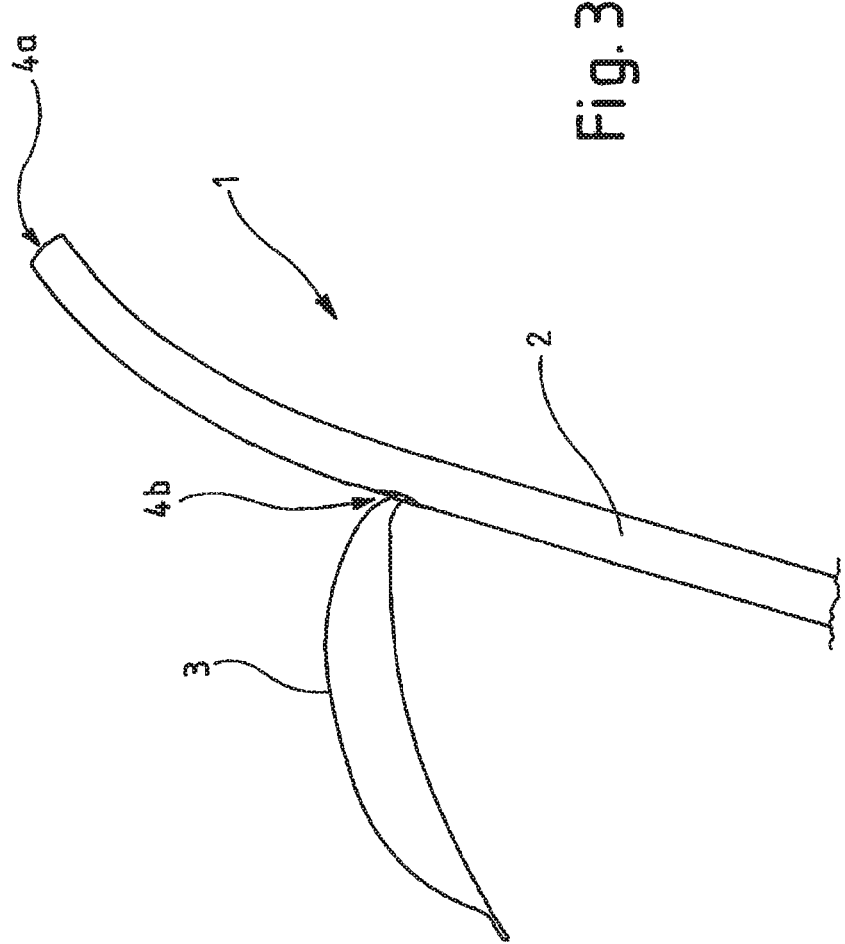
FIG. 3 is the inventive snare device with a partly emerged snare out of the lateral outlet opening of the catheter.
Figure 4:
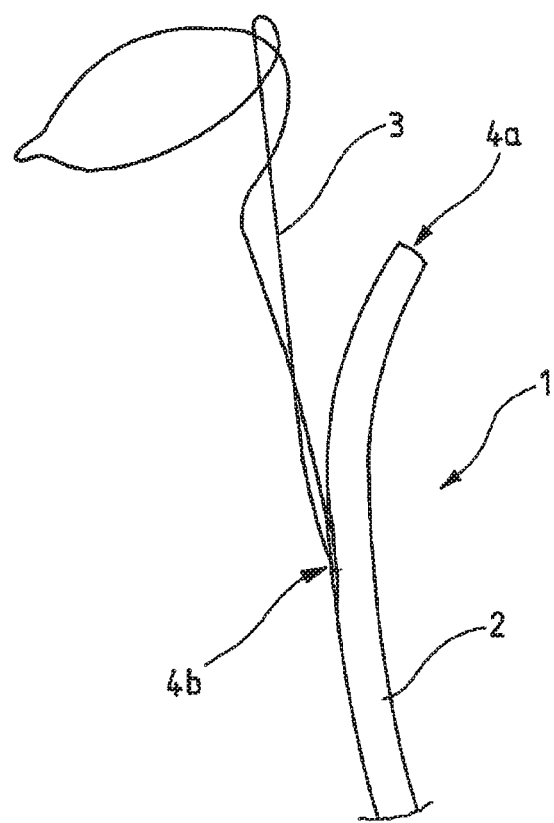
FIG. 4 is the embodiment of the inventive snare device with a snare that is completely emerged out of the lateral outlet opening of the catheter.

As shown in FIG. 3, the snare (3) is partially emerged out of the lateral outlet opening (4b). If the snare (3) is moved by the torquer such that the snare (3) emerges further out of the catheter (2), the snare (3) returns to its memorizes original shape, which is shown in FIG. 4. The snare (3) is now completely emerged out of the lateral outlet opening (4b) of the catheter (2).

Figure 5:
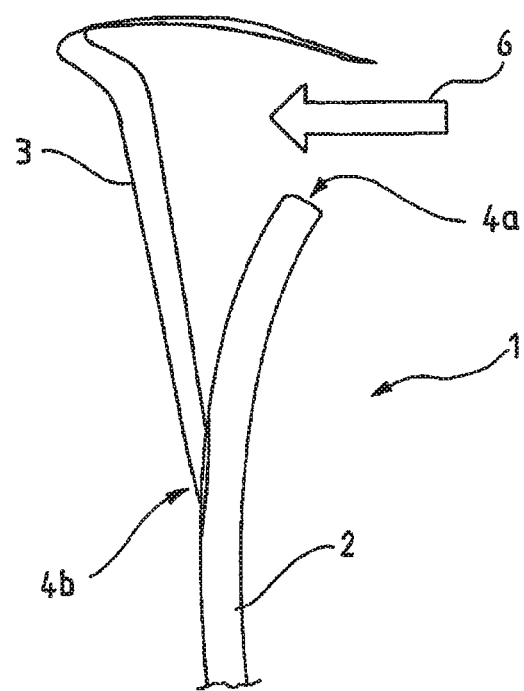
FIG. 5 is the snare device according to FIG. 4, wherein the snare is rotated by 180° in relation to the catheter.

To allow a catching of objects, which ends are non-probable, the snare must be rotated by 180° relative to the catheter (2) by manipulation at the torquer. This is illustrated in FIG. 5.

In order to realize the catching, the foreign body (5) to be caught is positioned between the distal end of the catheter (2) and the angled proximal portion of the snare (3). This is shown by the arrow (6).

Figure 6:
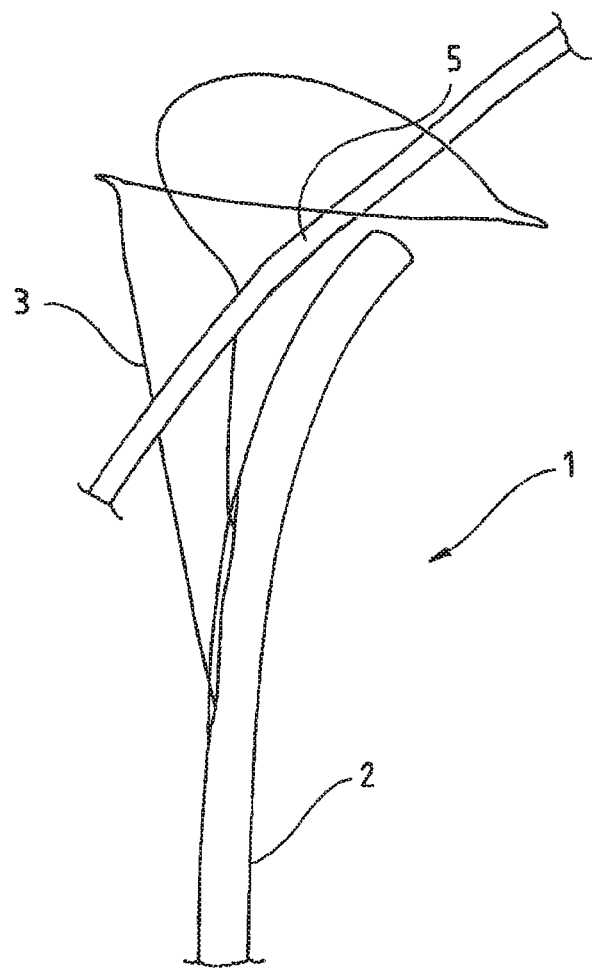
FIG. 6 is the snare device according to FIG. 5, wherein the snare is partly pulled into the catheter

If the foreign body (5) to be caught is positioned between the distal end of the catheter (2) and the angled portion of the snare (3), the snare (3) is pulled back into the catheter (2) slowly by manipulation at the torquer, wherein the angled proximal portion of the snare (3) lays over the distal end of the catheter (2). FIG. 6 shows this step of the catching.

The foreign body (5) to be caught, which ends are non-probable, is arranged between the distal end of the catheter (2) and the angled proximal portion of the snare (3). The angled proximal portion of the snare (3) is orientated relative to the catheter (2) in such a manner that it is put over the distal end of the catheter (2) by the back-pulling of the snare (3) into the catheter (2) by a manipulation with the torquer. Thus, the foreign body (5) is enclosed by the snare (3) and the catheter (2).

Figure 7A:
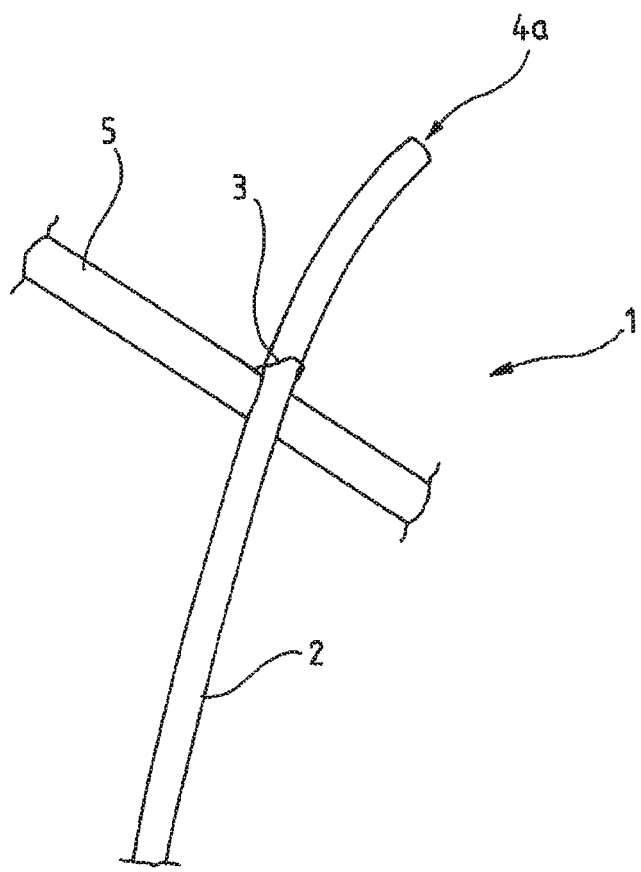

In FIG. 7a is shown that the foreign body (5), at hand represented by a catheter piece, is completely enclosed by the snare (3) and the catheter (2) so that it can be extracted, which is achieved by a back-pulling of the entire snare device (1). In contrast to FIG. 7a, FIG. 7b shows the catching to the foreign body (5) in a view from the front.

The lateral outlet opening (4b) of the catheter is recognizable. The snare (3) is pulled back into the catheter (2) such that the caught foreign body (5) is completely enclosed by the snare (3) and the catheter (2) and is held.

The embodiment illustrated and described in the drawing of the figures is merely for the purpose of explanation and is not restrictive for the invention.

REFERENCE NUMERALS 1 snare device
2 catheter
3 snare
4a outlet opening (positioned/distal at the end)
4b outlet opening (lateral)
5 foreign body
6 positioning of the foreign body

What is claimed is:

1. A snare device to catch an object or a foreign body in a human or an animal body, comprising:
   a hollow element, wherein the hollow element is a catheter, and
   a snare of a flexible elastic shape-memory material,
   wherein the snare is movable relative to the hollow element and is pullable into the hollow element and is pushable out of the hollow element,
   wherein the snare has a memorized original shape, to which the snare returns, when the snare is pushed out of the hollow element, by material stresses caused when the snare is pulled in,
   wherein the hollow element has an outlet opening, which is arranged laterally on the hollow element and which is set back from a distal end of the hollow element and through which the snare is pushable out of the hollow element and is pullable into the hollow element,
   wherein the snare is rotatable by 360° relative to the hollow element by a manipulation device,
   wherein the snare in the memorized original shape is formed such that an elongated proximal portion of the snare is angled in a predetermined angle,
   wherein the snare comprises a loop defining a loop opening,
   wherein the snare device is configured to catch the object or the foreign body between the loop and the hollow element, with the hollow element passing through the loop opening defined by the loop, and without the object or the foreign body passing through the loop opening defined by the loop.

2. The snare device according to claim 1, wherein the manipulation device is a torquer, which is arranged at a proximal end of the snare.

3. The snare device according to claim 1, wherein the snare is pushable out of the hollow element and is pullable into the hollow element by the manipulation device.

4. The snare device according to claim 1, wherein the lateral outlet opening of the hollow element is set back from the distal end of the hollow element in a range of 1 cm to 3 cm.

5. The snare device according to claim 4, wherein the lateral outlet opening of the hollow element is set back 2 cm from the distal end of the hollow element.

6. The snare device according to claim 1, wherein the lateral outlet opening of the hollow element is formed in a shape of an elongated slot.

7. The snare device according to claim 1, wherein the shape-memory material of the snare is formed of at least one of metal or plastic.

8. The snare device according to claim 7, wherein the shape-memory material is formed of nitinol.

9. The snare device according to claim 1, wherein the hollow element has a diameter in a range of 2 French to 8 French.

10. The snare device according to claim 9, wherein the hollow element has a diameter in a range of 4 French to 6 French.

11. The snare device according to claim 1, wherein a marker is arranged at the snare to make the snare visible under at least one displaying device.

12. A medical device, comprising:
   a snare device configured to catch an object or a foreign body in a human or an animal body, wherein the object or the foreign body has no free accessible end,
   the snare device comprising a hollow element, wherein the hollow element is a catheter, and a snare of a flexible elastic shape-memory material,
   wherein the snare is movable relative to the hollow element and is pullable into the hollow element and is pushable out of the hollow element,
   wherein the snare has a memorized original shape, to which the snare returns, when the snare is pushed out of the hollow element, by material stresses caused when the snare is pulled in,
   wherein the hollow element has an outlet opening, which is arranged laterally on the hollow element and which is set back from a distal end of the hollow element and through which the snare is pushable out of the hollow element and is pullable into the hollow element, wherein the snare comprises a loop defining a loop opening, wherein the snare device is configured to catch the object or the foreign body between the loop and the hollow element, with the hollow element passing through the loop opening defined by the loop, and without the object or the foreign body passing through the loop opening defined by the loop.

13. The snare device according to claim 12, wherein the snare is rotatable by 360° relative to the hollow element by a manipulation device.

14. The snare device according to claim 13, wherein the snare is pushable out of the hollow element and is pullable into the hollow element by the manipulation device.

15. The snare device according to claim 12, wherein the lateral outlet opening of the hollow element is set back from the distal end of the hollow element in a range of 1 cm to 3 cm.

16. The snare device according to claim 12, wherein the lateral outlet opening of the hollow element is formed in a shape of an elongated slot.

17. The snare device according to claim 12, wherein the shape-memory material of the snare is formed of at least one of metal or plastic.

18. The snare device according to claim 12, wherein the hollow element has a diameter in a range of 2 French to 8 French.

19. The snare device according to claim 12, wherein a marker is arranged at the snare to make the snare visible under at least one displaying device.

* * * * *